US00PP08969P

United States Patent [19]

Bradford et al.

[11] Patent Number: Plant 8,969

[45] Date of Patent: Nov. 8, 1994

[54] PLUM TREE (BRADPRUNE)

[76] Inventors: Lowell G. Bradford, 12439 E. Savana Rd.; Norman G. Bradford, 11875 E. Savana Rd., both of Le Grand, Calif. 95333

[21] Appl. No.: 199,841

[22] Filed: Feb. 22, 1994

[51] Int. Cl.[5] ..... A01H 5/00
[52] U.S. Cl. ..... Plt./38.2
[58] Field of Search ..... Plt. 38.1, 38.2

*Primary Examiner*—James R. Feyrer

[57] ABSTRACT

The present invention relates to a plum tree and more particularly to a new and distinct variety broadly characterized by a large size, vigorous, and medium productive tree, which requires cross pollinization. The fruit matures under the ecological conditions described in early August, with first picking on Aug. 3, 1993, and is uniformly large in size, semi-freestone in type, very dark red in skin color, oblong in shape, deliciously sweet in flavor, and firm in texture. The variety was developed as an open pollinated seedling of an unnamed seedling.

1 Drawing Sheet

BACKGROUND OF THE NEW VARIETY

In a continuing effort to improve the quality of shipping fruits, we, the inventors, typically hybridize a large number of nectarine, peach, plum, apricot, and cherry seedlings each year. The present invention relates to a new and distinct variety of plum tree, which has been denominated varietally as "Bradprune". Each year we grow a large number of seeds from selected seed parents that have been hybridized by selected pollen parents. We also grow a large number of seeds from selected seed parents that were open pollinated by unknown pollen sources. The present variety was developed by us in 1982, and the resulting seedling was planted in a cultivated area of our experimental orchard at Bradford Farms near Le Grand, Calif. in Merced County (San Joaquin Valley). Specifically, this seedling was originated by growing an open pollinated seed of an unnamed plum seedling. Subsequent to origination of the present variety of plum tree, we asexually reproduced it by budding and grafting, and such reproduction of plant and fruit characteristics were true to the original plant in all respects.

The present variety is most similar to the Grand Rosa (U.S. Plant Pat. No. 1,756) plum by producing large, semi-freestone, red fruit that matures in early August, but is distinguished therefrom and an improvement thereon by producing fruit that is darker red in skin color, that is smoother in skin texture, that is oblong in shape, that is less susceptible to growth cracking, and that is substantially sweeter in flavor.

DRAWING

The accompanying photograph exhibits four whole fruits positioned to display the characteristics of the skin color and form, one fruit divided around the suture plants to reveal the flesh, stone, and stone cavity; and several leaves, all typical of the subject variety.

POMOLOGICAL CHARACTERISTICS

Referring now more specifically to the pomological characteristics of this new and distinct variety of plum tree, the following has been observed under the ecological conditions prevailing at the experimental orchard of the inventors near Le Grand, Merced County (San Joaquin Valley), Calif., and was developed at the state of hard eating ripe on Aug. 12, 1993. All major color code designations are by reference to the Inter-Society Color Council, National Bureau of Standards. Common color names are also used occasionally.

TREE

Size: Large.
Vigor: Vigorous.
Growth: Upright and dense.
Form: Vase formed.
Hardiness: Hardy.
Production: Medium productivity.
Bearing: Uncertain bearer, self unfruitful, needs cross pollinating.
Trunk:
- *Size.*—Medium.
- *Texture.*—Shaggy.
- *Bark color.*—Brownish gray [64. brGy].
- *Lenticles.*—Numerous. Color: Brownish orange [54. brO]. Average size: ¼" [6.4 mm.].

Branches:
- *Size.*—Medium.
- *Texture.*—Medium to slightly shaggy.
- *Color.*—1st year wood topside: Light grayish red [18. l.gy.R]. 1st year wood underside: Moderate yellow green [120. m.YG]. Older wood: Grayish brown [61. gy.Br].
- *Lenticels.*—Very numerous. Color: Brownish orange [54. BrO]. Average size: 1/16" [1.6 mm.].

Leaves:
- *Size.*—Medium. Average length: 4½" [114.3 mm.]. Average width: 2⅜" [60.3 mm.].
- *Thickness.*—Medium.
- *Form.*—Oval.
- *Apex.*—Mucronate.
- *Base.*—Acute.
- *Surface.*—Smooth.
- *Color.*—Dorsal surface: Dark olive green [126. d.OlG]. Ventral surface: Moderate yellow green [120. m.YG].
- *Margin.*—Finely serrate.
- *Venation.*—Pinnately net veined.
- *Petiole.*—Average length: ¾" [19.1 mm.]. Average thickness: 1/16" [1.6 mm.]. Dorsal color: Moderate yellow green [120. m.YG]. Ventral color: Light yellow green [119. l.YG].

*Stipules.*—Numerous. Average length: 5/16" [7.9 mm.].

*Glands.*—Numbers: Mostly 2 to 4 per leaf. Position: Mostly oppositely positioned on petiole and base of blade. Size: Medium. Form: Globose. Color: Dark brown [59. d.Br].

Flower buds:

*Hardiness.*—Half hardy.

*Size.*—Medium.

*Length.*—Medium.

*Form.*—Free.

*Surface.*—Pubescent.

Flowers:

*Blooming period.*—Medium as compared with other varieties.

*Size.*—Medium.

*Color.*—White [263. White].

FRUIT

Maturity when described: Firm ripe, Aug. 13, 1993.

Date of first picking: Aug. 4, 1993.

Date of last picking: Aug. 18, 1993.

Size: Uniform, large.

*Average diameter axially.*—2⅛" [54.0 mm].

*Average traversely in suture plane.*—2⅝" [66.7 mm].

Form: Uniform, symmetrical, oblong.

*Longitudinal section form.*—Oval.

*Transverse section through diameter.*—Round.

Suture: An inconspicuous line extending from the base but discontinuing at the apex, with a slight depression just beyond the pistil point.

Ventral surface: Rounded.

Lips: Equally lipped very slightly toward apex.

Cavity: Flaring, circular in the suture plane, suture showing on one side only.

Base: Rounded.

Apex: Slightly mammiform, some rounded and some slightly pointed.

Pistil point: An inconspicuous dot at the end of the suture line.

Stem: Small.

*Average length.*—½" [12.7 mm.].

*Average width.*—⅛" [3.2 mm.].

Skin:

*Thickness.*—Medium.

*Texture.*—Medium.

*Tenacity.*—Tenacious to flesh.

*Tendency to crack.*—Very slight.

*Color.*—Very dark red [17. v.d.R] near apex blending into deep reddish orange [36. deep rO] near stem with light orange yellow [70. l.OY] freckling throughout, increasing in size near base.

Flesh:

*Color.*—Light orange yellow [70. l.OY] to the stone.

*Surface of the pit cavity.*—Covered with very fine dark orange yellow [72. d.OY] fibers, with a characteristic void at the base of stone.

*Amygdalin.*—Wanting.

*Juice.*—Very abundant, very rich.

*Texture.*—Firm, fine, crisp.

*Fibers.*—Abundant, tough.

*Ripens.*—Even.

*Flavor.*—Abundantly sweet with slight acid.

*Aroma.*—Very slight.

*Eating quality.*—Best, even when picked prematurely.

STONE

Type: Semi-freestone.

Form: Elliptical.

Base: Slightly oblique.

Apex: Acuminate.

Sides: Equal, flattened.

Surface: Rough, no pitting, with a groove along the dorsal fin.

Color: Moderate orange yellow [71. m.OY].

Average pit wall thickness: 1/16" [1.6 mm.].

Tendency to split: Very slight.

Kernel:

*Form.*—Oblong.

*Taste.*—Very bitter.

*Viable.*—Yes.

*Average width.*—⅜" [9.5 mm.].

*Average length.*—¾" [19.1 mm.].

Skin color: Pale yellow [89. p.Y] when first cracked.

Pellicle color: Dark grayish yellow [91. d.gy.Y].

Amygdalin: Abundant.

USE

Market: Fresh and long distance shipping.

Keeping quality: Excellent.

Shipping quality: Excellent.

Resistance to insects: No unusual susceptibilities noted.

Resistance to diseases: No unusual susceptibilities noted.

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, substantially as illustrated and described, that is most similar to the Grand Rosa (U.S. Plant Pat. No. 1,756) plum by producing large, semi-freestone, red fruit that matures in early August, but is distinguished therefrom and an improvement thereon by producing fruit that is darker red in skin color, that is smoother in skin texture, that is oblong in shape, that is less susceptible to growth cracking, and that is substantially sweeter in flavor.

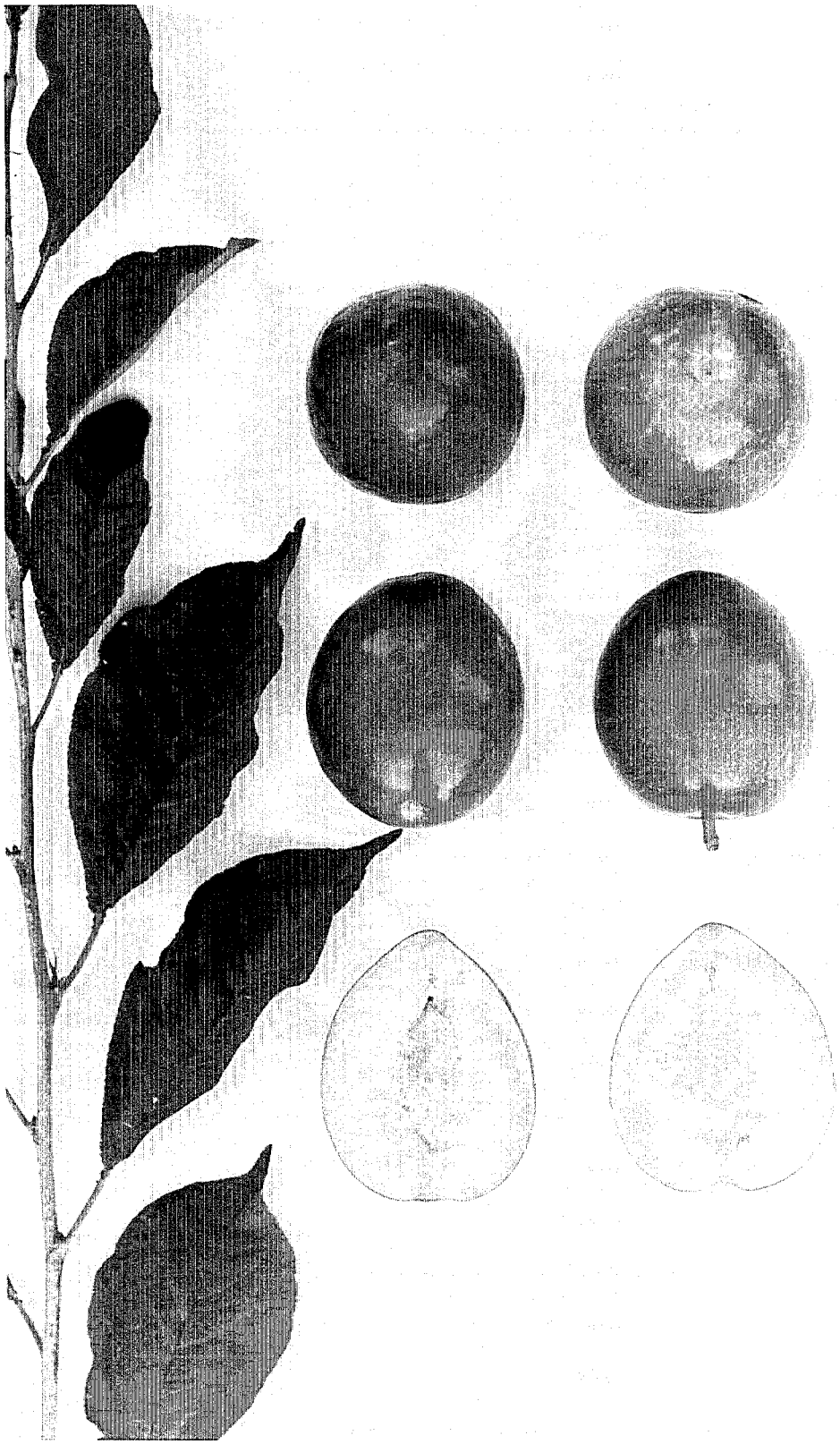

* * * * *